US00PP11311P

United States Patent [19]

Cotta

[11] Patent Number: Plant 11,311

[45] Date of Patent: Mar. 21, 2000

[54] RHODODENDRON PLANT NAMED 'AMY COTTA'

[76] Inventor: Steve P. Cotta, 33 Duggan Rd., Tiverton, R.I. 02878

[21] Appl. No.: 09/106,062

[22] Filed: Jun. 29, 1998

[51] Int. Cl.[7] ..... A01H 5/00

[52] U.S. Cl. ..... Plt./238

[58] Field of Search ..... Plt./238, 239, 240

[56] References Cited

PUBLICATIONS

The RHS Dictionary of Gardening, A. Huxley (Ed. in Chief), The MacMillan Press Limited, London, pp. 30–31, 1992.

Plant Systematics, Jones and Luchsinger, McGraw–Hill, Inc., U.S.A., p. 60, 1986.

*Primary Examiner*—Howard J. Locker
*Assistant Examiner*—Anne Marie Grünberg
*Attorney, Agent, or Firm*—C. A. Whealy

[57] ABSTRACT

A new and distinct cultivar of Rhododendron plant named 'Amy Cotta', characterized by its compact, slow-growing, dense plants that are very freely branching; very uniform, symmetrical, rounded plant habit; dark green small leaves; uniform flowering; numerous, showy, ruffled, small lavender pink flowers; good weather-tolerance; and hardy to zone 4.

2 Drawing Sheets

BACKGROUND OF THE INVENTION

The present invention relates to a new and distinct cultivar of evergreen Rhododendron, botanically known as *Rhododendron minus carolinianum×dauricum sempervirens* and hereinafter referred to by the name 'Amy Cotta'.

The new Rhododendron is a naturally-occurring mutation of the *Rhododendron minus caroliniarum×Dauricum sempervirens* cultivar PJM (not patented). The new Rhododendron was discovered and selected by the inventor as a single plant within a large population of plants of the parent cultivar, the *Rhododendron minus carolinianum×dauricum sempervirens* cultivar PJM, in a controlled environment in Portsmouth, R.I., in 1982. The selection of this plant was based on its smaller leaf size, denser growth habit and slower growth rate.

Asexual reproduction of the new Rhododendron by terminal cuttings taken in a controlled environment in Portsmouth, R.I., has shown that the unique features of this new Rhododendron are stable and reproduced true to type in successive generations.

BRIEF SUMMARY OF THE INVENTION

The new Rhododendron has not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Amy Cotta'. These characteristics in combination distinguish 'Amy Cotta' as a new and distinct cultivar:

1. Compact, slow-growing, dense plants that are very freely branching.
2. Very uniform, symmetrical, rounded plant habit.
3. Dark green small leaves.
4. Uniform flowering.
5. Numerous, showy, ruffled, small lavender pink flowers.
6. Good weather-tolerance, hardy to zone 4.

Plants of the new Rhododendron can be compared to plants of the parent cultivar PJM. However, in side-by-side comparisons conducted in Portsmouth, R.I., plants of the new Rhododendron differ from plants of the cultivar PJM in the following characteristics:

1. Plants of the new Rhododendron are slower-growing and more compact than plants of the cultivar PJM.
2. Leaves of plants of the new Rhododendron are much smaller and darker in color than leaves of plants of the cultivar PJM.
3. Plants of the new Rhododendron are more uniform, rounded and denser than plants of the cultivar PJM.
4. Plants of the new Rhododendron retain the lower branches and foliage better than plants of the cultivar PJM.

BRIEF DESCRIPTION OF THE PHOTOGRAPHS

The accompanying colored photographs illustrate the overall appearance of the new Rhododendron, showing the colors as true as it is reasonably possible to obtain in colored reproductions of this type. The photograph on the first sheet comprises a side perspective view of typical plant of 'Amy Cotta' in full flower. The photograph on the second sheet comprises a top perspective view of typical plants of 'Amy Cotta' (left) and 'PJM' (right) showing the differences in growth habit and size. Flower and foliage colors in the photographs may appear different from the actual colors due to light reflectance.

DETAILED BOTANICAL DESCRIPTION

The aforementioned and following observations, measurements, values, and comparisons describe plants grown in Portsmouth, R.I., and Roanoke, Tex., under outdoor conditions which closely approximate commercial production conditions. Plants used for the description were approximately five years old.

In the following description, color references are made to The Royal Horticultural Society Colour Chart except where general terms of ordinary dictionary significance are used.

Botanical classification: *Rhododendron minus carolinianum×dauricum sempervirens 'Amy Cotta'*.

Parentage: Naturally-occurring mutation of *Rhododendron minus caroliniarum×dauricum sempervirens* 'PJM'.

Propagation:

*Type.*—By terminal cuttings.

*Time to initiate roots.*—About 25 days at temperatures of 24° C.

*Time to develop roots.*—About 80 days at temperatures of 24° C.

*Rooting habit.*—Very fine, finely-branched.

Plant description:

*Plant form and growth habit.*—Perennial, dense and rounded, very uniform and symmetrical plant habit. Moderate vigor. In early spring, numerous flowers per plant.

*Branching habit.*—Very freely branching.

*Plant height, soil level to top of flowers.*—About 44 cm.

*Plant diameter, area of spread.*—About 52 cm.

*Lateral branch description.*—Length: About 15 cm. Diameter: About 4 mm. Color: Gray, 197A, to brown, 173A. Texture: Immature stems, pubescent.

Foliage description:

*Arrangement.*—Alternate, single.

*Length.*—About 3.2 cm.

*Width.*—About 1.75 cm.

*Shape.*—Elliptic.

*Apex.*—Acute or slightly retuse.

*Base.*—Cuneate.

*Margin.*—Entire.

*Texture.*—Leathery, slight pubescence on midvein towards base of upper surface of leaves.

*Color.*—Young foliage, upper surface: Dark green, darker than 147A. Young foliage, lower surface: Close to 147B. Mature foliage, upper surface: Dark green, darker than 147A. Mature foliage, lower surface: 147B.

*Petiole.*—Length: About 6 mm. Diameter: About 1 mm. Color: 144A.

Flower description:

*Natural flowering season.*—Spring after sufficient cool period. Early flowering; in the Northeast, bloom date is typically mid to late April.

*Flower arrangement.*—Flowers arranged at terminals in clusters of three to four with usually about nine to twelve flowers per apex. Flowers face upward and outward. Very freely flowering.

*Flower appearance.*—Single flowers. Lavender pink petals with lighter lavender to white throat. Flowers persistent. Flowers not fragrant.

*Flower diameter.*—About 4 cm.

*Flower height.*—About 2.5 cm.

*Postproduction longevity.*—About twelve days depending on temperature and precipitation.

*Flower bud (just starting to show petal color).*—Length: About 1 cm. Diameter: About 7 mm. Shape: Ovoid.

*Petals.*—Appearance: Satiny. Texture: Smooth. Arrangement: Small single flowers. Corolla consists of five fused petals. Shape: Elliptic with rounded apex. Margin: Entire with undulating edge which gives a ruffled appearance. Length: About 2.5 cm. Width: About 1.5 cm. Color: When opening, upper and lower surfaces: Close to 75A-75B. Fully opened, upper and lower surfaces: Close to 75A-75D. Throat: 75D to white.

*Peduncles.*—Length: About 1.25 cm. Angle: Upright. Strength: Flexible, strong. Color: 144A-144B.

*Reproductive organs.*—Androecium: Stamen number: Usually ten, whiskered at base. Stamen length: About 2 cm. Filament color: White. Anther shape: Oblong. Anther size: About 2 mm by 1 mm. Anther color: Close to 90B, blue violet. Amount of pollen: Moderate. Pollen color: Light greenish yellow to light yellow.

*Gynoecium.*—Pistil length: About 2.1 cm. Stigma shape: Rounded. Style color: Dark pink, close to 57C. Ovary color: Close to 139B.

Disease resistance: No known Rhododendron diseases observed to date on plants grown under commercial greenhouse conditions.

Seed production: Seed production has not been observed.

It is claimed:

1. A new and distinct Rhododenron plant named 'Amy Cotta', as illustrated and described.

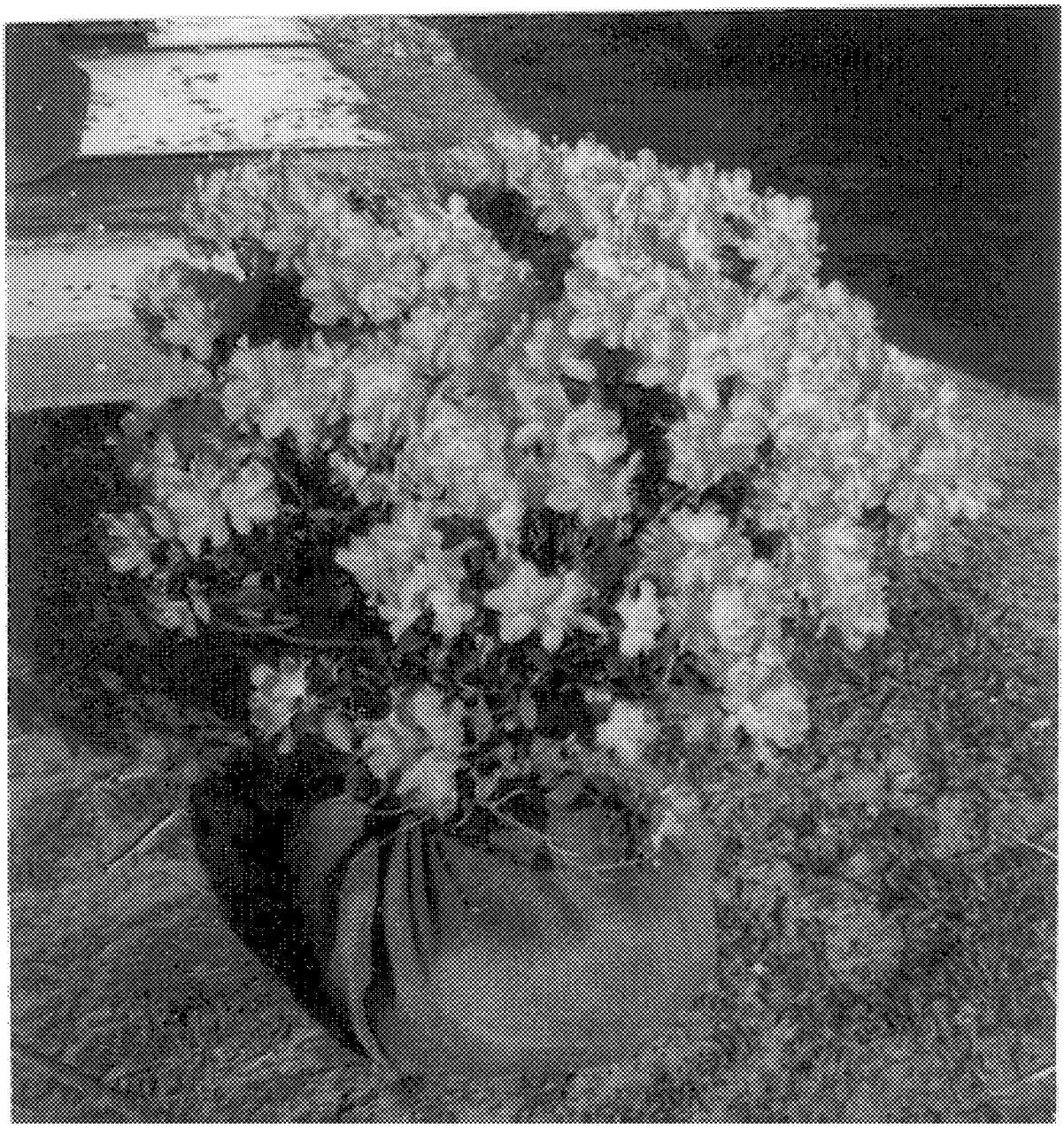

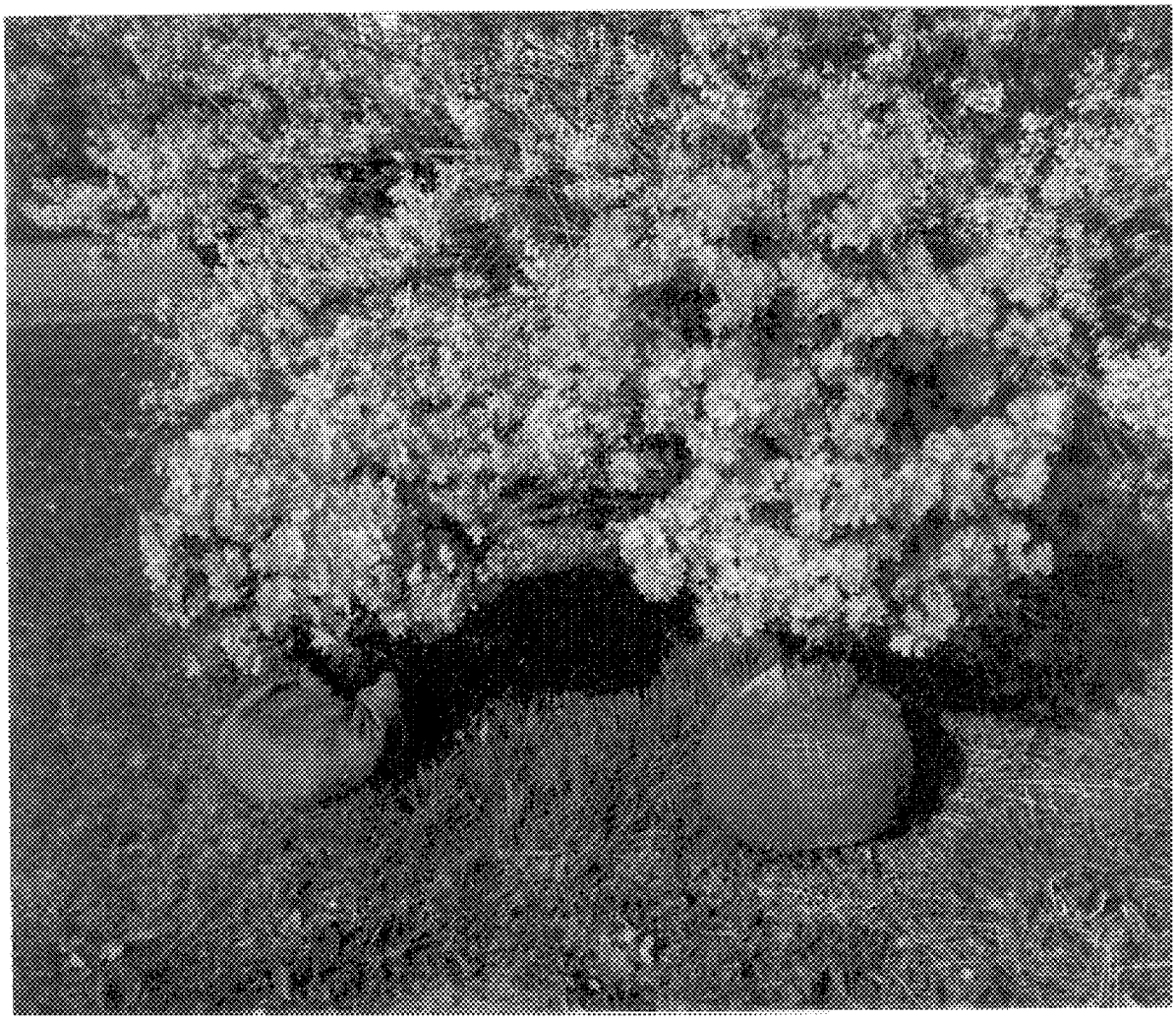

* * * * *